United States Patent [19]
Henry et al.

[11] Patent Number: 6,121,269
[45] Date of Patent: Sep. 19, 2000

[54] REDUCTION OF HAIR GROWTH

[76] Inventors: James P. Henry, 10257 Meadow Fence Ct., Myersville, Md. 21773; Gurpreet S. Ahluwalia, 8632 Stableview Ct., Gaithersburg, Md. 20852

[21] Appl. No.: 09/255,063

[22] Filed: Feb. 22, 1999

[51] Int. Cl.$^7$ .................................................. A61K 31/505
[52] U.S. Cl. ........................ 514/259; 514/295; 514/415; 514/520; 514/535; 514/567; 514/629
[58] Field of Search .................................. 514/259, 295, 514/415, 520, 535, 567, 629

[56] References Cited

U.S. PATENT DOCUMENTS

| | | |
|---|---|---|
| 3,426,137 | 2/1969 | Philpitt et al. |
| 4,039,669 | 8/1977 | Beylar et al. |
| 4,139,638 | 2/1979 | Neri et al. |
| 4,161,540 | 7/1979 | Neri et al. |
| 4,191,775 | 3/1980 | Glen . |
| 4,269,831 | 5/1981 | Ferrari et al. |
| 4,370,315 | 1/1983 | Greff et al. |
| 4,439,432 | 3/1984 | Peat . |
| 4,508,714 | 4/1985 | Cecic et al. |
| 4,517,175 | 5/1985 | Iwabuchi et al. |
| 4,720,489 | 1/1988 | Shander . |
| 4,885,289 | 12/1989 | Breuer et al. |
| 4,935,231 | 6/1990 | Pigiet . |
| 5,095,007 | 3/1992 | Ahluwalia . |
| 5,096,911 | 3/1992 | Ahluwalia et al. |
| 5,132,293 | 7/1992 | Shander et al. |
| 5,143,925 | 9/1992 | Shander et al. |
| 5,189,212 | 2/1993 | Ruenitz . |
| 5,271,942 | 12/1993 | Haverhagen . |
| 5,300,284 | 4/1994 | Wiechers et al. |
| 5,328,686 | 7/1994 | Shander et al. |
| 5,362,748 | 11/1994 | Schwen et al. |
| 5,364,885 | 11/1994 | Ahluwalia et al. |
| 5,411,991 | 5/1995 | Shander et al. |
| 5,444,090 | 8/1995 | Ahluwalia et al. |
| 5,455,234 | 10/1995 | Ahluwalia et al. |
| 5,468,476 | 11/1995 | Ahluwalia et al. |
| 5,474,763 | 12/1995 | Shander et al. |
| 5,554,608 | 9/1996 | Ahluwalia et al. |
| 5,645,825 | 7/1997 | Hillebrand et al. |
| 5,648,394 | 7/1997 | Boxall et al. |
| 5,652,273 | 7/1997 | Henry et al. |
| 5,674,477 | 10/1997 | Ahluwalia . |
| 5,728,736 | 3/1998 | Shander et al. |
| 5,776,442 | 7/1998 | Ahluwalia . |
| 5,824,665 | 10/1998 | Henry et al. |
| 5,840,752 | 11/1998 | Henry et al. |
| 5,959,213 | 9/1999 | Harmon et al. |

FOREIGN PATENT DOCUMENTS

| | | |
|---|---|---|
| 0 413 528 A1 | 2/1991 | European Pat. Off. |
| 0 532 219 A2 | 3/1993 | European Pat. Off. |
| 1 458 349 | 12/1976 | United Kingdom . |
| WO 98/02134 | 1/1998 | WIPO . |

OTHER PUBLICATIONS

Botchkarev et al., "A New Role for Neurotrophin–3 Involvement in the Regulation of Hair Follicle Regression (Catagen)", American Journal of Pathology, vol. 153, No. 3, Sep. 1998.

Botchkarev et al., "Neurotrophin–3 Involvement in the Regulation of Hair Follicle Morphogenesis", The Journal of Investigative Dermatology, vol. 111, No. 2, Aug. 1998.

Hoffman et al., "Interleukin–1β–Induced Inhibition of Hair Growth In Vitro Is Mediated by Cyclic AMP", The Journal of Investigative Dermatology, vol. 108, No. 1, Jan. 1997.

Malarkey et al., "The regulation of tyrosine kinase signalling pathways by growth factor and G–protein–coupled receptors", Biochem. J., 1995.

Thompson et al., "Tyrosine Kinase Inhibitors. 2. Synthesis of 2.2'–Dithiobis(1H–indole–3–alkanamides) and Investigation of Their Inhibitory Activity against Epidermal Growth Factor Receptor . . . ", J. Med. Chem. 1994.

Weinberg et al., "Reconstitution of Hair Follicle Development In Vivo: Determination of Follicle Formation, Hair Growth, and Hair Quality by Dermal Cells", The J. of Invest. Dermatology, vol. 100, No. 3, Mar. 1993.

Thompson et al., "Tyrosine Kinase Inhibitors. 1. Structure–Activity Relationships for Inhibition of Epidermal Growth Factor Receptor Tyrosine Kinase Activity by 2,3–Dihydro–2–thioxo–1H–indole–3–. . . ", J. Med. Chem. 1993.

Andrew G. Messenger, "The Control of Hair Growth: An Overview", The Society for Investigative Dermatology, Inc., 1993.

Alexander Levitzki, "Tyrphostins: tyrosine kinase blockers as novel antiproliferative agents and dissectors of signal transduction", The FASEB Journal, vol. 6, Nov. 1992.

Terrence R. Burke, Jr., "Protein–tyrosine kinase inhibitors", Drugs of the Future, 1992.

John E. Casnellie, "Protein Kinase Inhibitors: Probes for the Functions of Protein Phosphorylation", Advances in Pharmacology, vol. 22, 1991.

Traxler et al., "Sulfonylbenzoyl–Nitrostyrenes: Potential Bisubstrate Type Inhibitors of the EGF–Receptor Tyrosine Protein Kinase", J. Med. Chem., vol. 34, No. 8, 1991.

Geahlen et al., "Piceatannol (3,4,3',5'–Tetrahydroxy–Trans–Stilbene) Is a Naturally Occurring Protein–Tyrosine Kinase Inhibitor", Biochemical and Biophysical Research Communications, vol. 165, No. 1, Nov. 1989.

Hattori et al., "Biochemical Analysis of Hair Growth from the Aspects of Aging and Enzyme Activities", The Journal of Dermatology, vol. 10, 1983.

Styczynski et al., "Reduction of Hair Growth", U.S. Serial No. 09/179,267, filed Oct. 27, 1998.

Styczynski et al., "Reduction of Hair Growth", U.S. Serial No. 09/010,227, filed Jan. 21, 1998.

Styczynski et al., "Modulation of Hair Growth", U.S. Serial No. 09/009,213, filed Jan. 20, 1998.

Henry et al., "Reduction of Hair Growth", U.S. Serial No. 08,935, 181, filed Sep. 22, 1997.

*Primary Examiner*—Rebecca Cook
*Attorney, Agent, or Firm*—Fish & Richardson P.C.

[57] ABSTRACT

Mammalian hair growth is reduced by applying to the skin an inhibitor of protein-tyrosine kinase.

46 Claims, No Drawings

REDUCTION OF HAIR GROWTH

BACKGROUND OF THE INVENTION

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic anti-androgens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

Protein-tyrosine kinases (PTKs) are a class of enzymes that catalyze the transfer of the terminal phosphate from adenosine triphosphate (ATP) to the phenolic hydroxyl group of the amino acid tyrosine in substrate proteins (Malarkey et. al., Biochem. J. 309:361–375, 1995). These enzymes are normally present in one of two forms, a transmembrane receptor that binds growth factors and a cytoplasmic kinase that is involved in the signal transduction from other receptors.

Many transmembrane growth factor receptors possess PTK activity. Initiation of this activity following binding of an extracellular growth factor is the first step in cellular signal transduction pathway. The initial activation of the receptor protein-tyrosine kinase after a growth factor binding is manifested by autophosphorylation, which may cause conformational alterations exposing the active site to external substrates. This substrate activation in turn transmits the signal downstream. The binding of epidermal growth factor (EGF) at the extracellular binding domain is an example of the signaling process.

Central to the function of protein-tyrosine kinases is the recognition and binding of a nucleoside triphosphate (usually ATP), and a tyrosyl containing protein substrate. Several classes of protein kinase inhibitors have been described (Casnellie, Advances in Pharmacology 22:167–205, 1991; Burke, Drugs of the Future 17:119–131, 1992). They include agents that prevent the nucleotide (e.g., ATP) binding to PTKs; that prevent the substrate binding at the peptide binding site; and agents that decrease the catalytic efficiency by some other mechanism, e.g., binding to the allosteric regulatory site.

SUMMARY OF THE INVENTION

The invention features reducing unwanted mammalian (including human) hair growth—particularly androgen-stimulated hair growth—by applying to the skin a composition including an inhibitor of protein-tyrosine kinases in an amount effective to reduce hair growth. The unwanted hair growth which is reduced may be normal hair growth, or hair growth that results from an abnormal or diseased condition.

Other features and advantages of the invention may be apparent from the description of the preferred embodiments thereof, and from the claims.

DESCRIPTION OF THE PREFERRED EMBODIMENTS

The preferred composition includes at least one inhibitor of protein-tyrosine kinase in a cosmetically and/or dermatologically acceptable vehicle. The composition may be a solid, semi-solid, or liquid. The composition may be, for example, a cosmetic and dermatologic product in the form of an, for example, ointment, lotion, foam, cream, gel, or hydroalcoholic solution. The composition may also be in the form of a shaving preparation or an aftershave. The vehicle itself can be inert or it can possess cosmetic, physiological and/or pharmaceutical benefits of its own.

Inhibitors of protein-tyrosine kinase may interfere with the nucleotide binding site on the enzyme or the peptide binding site on the enzyme, or may act by some other mechanism. An example of an inhibitor of protein-tyrosine kinase that interferes with the nucleotide binding site is lavendustin-A. (See Onoda et al.,) J. Nat. Prod., 52:1252–1257, 1989)).

Examples of inhibitors of protein-tyrosine kinase that interfere with the peptide binding site include erbstatin (Umegawa et al., J. Antibiot. 39:170–73, 1986), which inhibits EGF-receptor protein-tyrosine kinase; tryphostins, which are analogs of erbstatin (Levitzki, FASEB J. 6:3275–3282, 1982); certain synthetic tetrahydroxy transsstilbene, or piceatannol (Geahlen, Biochem. and Biophy. Res. Commun. 165:241–245, 1999). The following are the chemical names of specific tryphostins that are inhibitors of protein-tyrosine kinase: 4-hydroxybenxylidenemalononitrile (tyrophostin A8); 3,5-di-t-butyl-4-hydroxybenzylidenemalononitrile (tyrophostin A9); α-cyano-(3,4-dihydroxy)cinnamonitrile (tyrophostin A23); α-cyano-(3,4,5-trihydroxy)cinnamonitrile (tyrophostin A25); α-cyano-(3,4-dihydroxy)cinnamide; (tyrophostin A46); α-cyano-(3,4-dihydroxy)thiocinnamide (tyrophostin A47); 2-amino-4-(4'-hydroxyphenyl)-1,1,3-tricyanobuta-1,3-diene (tyrophostin A48); 2-amino-4-(3',4',5'-trihydroxyphenyl)-1,1,3-tricyanobuta-1,3-diene (tyrophostin A51); 2-amino-4-(1H-indol-5-yl)-1,1,3- tricyanobuta-1,3-diene (tyrophostin AG 370); 4-hydroxy-3-methoxy-5-(benzothiazolythiomethyl) benzylidenecyanoacetamide (tyrophostin 825); 4-amino-N-(2,5-dihydroxybenzyl)methyl benzoate (tyrophostin AG 957); α-cyano-(3,4-dihydroxy)cinnamonitrile (tyrophostin AG 1288); 4-(3-Chloroanilino)-6,7-dimethoxyquinazoline (tyrophostin AG 1478); α-cyano-(3,4-dihydroxy)-N-benzylcinnamide (tyrophostin B42); (−)-R-N-(a-methylbenzyl)-3,4-dihdroxybenzylidenecyanoacetamide (tyrophostin B44(−)); α-cyano-(3,4-dihydroxy)-N-(3-phenylpropyl)cinnamide (tyrophostin B46); (tyrophostin B48: α-cyano-(3,4-dihydroxy)-N-phenylcinnamide; α-cyano-(+)-(S)-N-(α-phenethyl)-(3,4-dihydroxy) cinnamide (tyrophostin B50(+)); and α-cyano-(3,4-dihydroxy)-N-(phenylbutyl)cinnamide (tyrophostin B56).

Examples of inhibitors of protein-tyrosine kinase that work by some other mechanism include the benzoquinone ansamycin herbimycin A. Inactivation by this inhibitor involves steric hindrance of the active site rather than destruction of catalytic activity per se. Additional inhibitors include thiazolidine-diones, phenazocine, 2,3-dihydro-2-thioxo-1H-indole-3-alkanoic acids and their dimeric oxidation products, the 2,2'-dithiobis (1H)-indole-3-alkanoic acids) and sulfonylbenzoyl-nitrostyrenes (Thompson et. al., J. Med. Chem. 36:2459–2469, 1993; Thompson et. al., J. Med. Chem. 37:598–609, 1994; and Traxler et. al., J. Med. Chem. 34: 2328–2337, 1991).

The composition may include more than one inhibitor of protein-tyrosine kinase. In addition, the composition may include one or more other types of hair growth reducing agents, such as those described in U.S. Pat. No. 4,885,289; U.S. Pat. No. 4,720,489; U.S. Pat. No. 5,132,293; U.S. Pat. No. 5,096,911; U.S. Pat. No. 5,095,007; U.S. Pat. No. 5,143,925; U.S. Pat. No. 5,328,686; U.S. Pat. No. 5,440,090; U.S. Pat. No. 5,364,885; U.S. Pat. No. 5,411,991; U.S. Pat. No. 5,648,394; U.S. Pat. No. 5,468,476; U.S. Pat. No. 5,475,763; U.S. Pat. No. 5,554,608; U.S. Pat. No. 5,674,477; U.S. Pat. No. 5,728,736; U.S. Pat. No. 5,652,273; WO 94/27586; WO 94/27563; and WO 98/03149, all of which are incorporated herein by reference.

The concentration of the inhibitor of protein-tyrosine kinase in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. The effective amounts may range, for example, from 10 to 3000 micrograms or more per square centimeter of skin.

Vehicles can be formulated with liquid or solid emollients, solvents, thickeners, humectants and/or powders. Emollients include stearyl alcohol, mink oil, cetyl alcohol, oleyl alcohol, isopropyl laurate, polyethylene glycol, olive oil, petroleum jelly, palmitic acid, oleic acid, and myristyl myristate. Solvents may include ethyl alcohol, isopropanol, acetone, diethylene glycol, ethylene glycol, dimethyl sulfoxide, and dimethyl formamide.

The composition also may include components that enhance the penetration of the inhibitors of protein-tyrosine kinase into the skin and/or to the site of action. Examples of penetration enhancers include urea, polyoxyethylene ethers, terpenes, cis-fatty acids (oleic acid, palmitoleic acid), acetone, laurocapram, dimethylsulfoxide, 2-pyrrolidone, oleyl alcohol, glyceryl-3-stearate, cholesterol, myristic acid isopropyl ester, and propylene glycol.

The composition also can be formulated to provide a reservoir within or on the surface of the skin to provide for a continual slow release of the inhibitor. The composition also may be formulated to evaporate slowly from the skin, allowing the inhibitor extra time to penetrate the skin.

The following are examples of compositions including an inhibitor of protein-tyrosine kinase.

EXAMPLE 1

A composition contains 10% by weight of an inhibitor of protein-tyrosine kinase and 90% by weight of a vehicle containing water (68% of vehicle by weight), ethanol (16% of vehicle by weight), propylene glycol (5%, of the vehicle by weight), dipropylene glycol (5% of the vehicle by weight), benzyl alcohol (4% of the vehicle by weight) and propylene carbonate (2% of the vehicle by weight). The inhibitor can be, for example, a tyrophostin, erbstatin, lavendustin A, methyl caffeate, Herbimycin A, $HNMPA(AM)_3$—hydroxy-2-naphthalenylmethylphosphonic acid tris acetoxymethyl ester, or N-acetyl-Asp-Tyr-(2-malonyl)-Val-Pro-Met-Leu-$NH_2$.

EXAMPLE 2

A second composition contains 10% by weight of an inhibitor of protein-tyrosine kinase and 90% by weight of a vehicle containing water (80.84% by weight of the vehicle by weight of the vehicle), glyceryl stearate (4.24% by weight of the vehicle), polyethylene glycol 100-stearate (4.09% by weight of the vehicle), cetearyl alcohol (3.05% by weight of the vehicle), ceteareth-20 (2.5% by weight of the vehicle), mineral oil (2.22% by weight of the vehicle), stearyl alcohol (1.67% by weight of the vehicle), and dimethicone (0.56% by weight of the vehicle). The inhibitor can be, for example, a tyrophostin, erbstatin, lavendustin A, methyl caffeate, herbimycin A, $HNMPA(AM)_3$—hydroxy-2-naphthalenylmethylphosphonic acid tris acetoxymethyl ester, or N-acetyl-Asp-Tyr-(2-malonyl)-Val-Pro-Met-Leu-$NH_2$.

Optionally, one of the penetration enhancers mentioned previously may be added to the composition. A penetration enhancer could be added at concentrations of, for example, 0.13% to 20% by weight. The preferred concentration is 0.5% to 5% by weight.

The composition should be topically applied to a selected area of the body from which it is desired to reduce hair growth. For example, the composition can be applied to the face, particularly to the beard area of the face, i.e., the cheek, neck, upper lip, and chin. The composition also may be used as an adjunct to other methods of hair removal including shaving, waxing, mechanical epilation, chemical depilation, electrolysis and laser-assisted hair removal.

The composition can also be applied to the legs, arms, torso or armpits. The composition is particularly suitable for reducing the growth of unwanted hair in women suffering from hirsutism or other conditions. In humans, the composition should be applied once or twice a day, or even more frequently, to achieve a perceived reduction in hair growth. Perception of reduced hair growth could occur as early as 24 hours or 48 hours (for instance, between normal shaving intervals) following use or could take up to, for example, three months. Reduction in hair growth is demonstrated when, for example, the rate of hair growth is slowed, the need for removal is reduced, the subject perceives less hair on the treated site, or quantitatively, when the weight of hair removed (i.e., hair mass) is reduced.

Human Hair Follicle Growth Assay

The above-described assay will be referred to herein as the "Human Hair Follicle Growth Assay." Preferred compositions provide a reduction in hair growth of at least about 10%, more preferably at least about 40%, and most preferably at least about 70%.

In another experiment isolated hair follicles were exposed to either 1 mM or 0.01 mM concentration of the protein-tyrosine kinase inhibitor erbstatin, and the hair growth rate was compared to control. Measurements were made at days 0, 1 and 4. The results are as shown in Table 2.

TABLE 2

| Group | Pretreatment length (Day 0) | Posttreatment (Day-1) | | | Posttreatment (Day-4) | | |
|---|---|---|---|---|---|---|---|
| | | Length (mm) | Growth (mm) | Inhibition (%) | Length (mm) | Growth (mm) | Inhibition (%) |
| Control | 3.1 ± .17 | 3.7 ± .17 | 0.6 | 0.0 | 4.0 ± .16 | 0.9 | 0.0 |
| Erbstatin 1 mM | 3.0 ± .20 | 3.0 ± .17 | 0.0 | 100.0 | 3.3 ± .15 | 0.3 | 67 |
| Erbstatin 0.01 mM | 3.0 ± .23 | 3.1 ± .20 | 0.1 | 83.0 | 3.8 ± .29 | 0.8 | 11 |

Human hair follicles in growth phase (anagen) were isolated from face-lift tissue under a dissecting scope using a scalpel and watchmakers forceps. The skin was sliced into thin strips exposing 2–3 rows of follicles that could readily be dissected. Follicles were placed into 0.5 mL Williams E medium (Life Technologies, Gaithersburg, MD) supplemented with 2 mm L-glutamine, 10 μg/mL insulin, 10 ng/mL hydrocortisone, 100 units penicillin, 0.1 mg/mL streptomycin and 0.25 μg/mL amphotericin B. The follicles were incubated in 24 well plates (1 follicle/well) at 37° C. in an atmosphere of 5% $CO_2$ and 95% air. Hair follicles were videorecorded in the 24-well plates under the dissecting scope under a power of 20x. Hair follicle lengths were assessed using an image analysis software system (Computer Eyes and NIH Image). Typically, initial recordings were made on day 0 (day follicles were placed in culture), and on days 1, 4, and 7.

Inhibition of Human Hair Growth

The effect of five protein-tyrosine kinase inhibitors on human hair follicle growth was determined by exposing the isolated follicles to the enzyme inhibitors. The hair follicle lengths were determined before and after the inhibitor treatment. Typically, a set of 12 isolated follicles was used for determining the effect of each inhibitor on hair follicle growth. Hair growth reduction in the range of 40 to 100% was observed; the results are in shown in Table 1.

Protein-Tyrosine Kinase Assay

Protein-tyrosine kinase activity was measured in human skin samples rich in hair follicles using a commercially available assay kit (Calbiochem). Human skin obtained from a local plastic surgeon as a by-product of face-lift procedures was homogenized in four volumes of the extraction buffer containing 20 mM Tris-HCL, pH7.4, 50 mM NaCl, 1 mM EDTA, 1 mM EGTA, 5 mM mercaptoethanol. The samples were centrifuged for 10 min at 16,000×g to remove the membrane/organelle fractions. The supernatant fraction was used for the tyrosine kinase assay. Adding 25 ml of the 20x concentrated solution to 475 ml of deionized water and mixing made a working solution of plate wash buffer. The kinase buffer was prepared by adding 50 ul/ml of the 2 mM ATP stock solution to 1x sample buffer without 2-mercatoethanol. (90 ul of the kinase buffer/well). For the enzyme assay, 10 ul of each sample was added to a well. 10 ul of Abl standard, as positive controls, were added to a well. The kinase reaction was started by adding 90 ul of 1x kinase buffer/well and incubated at room temp for 30 minutes. The contents of each well was washed six times with 1x wash buffer, 100 ul of PY20 antibody diluted 1:200 with 1x Sample/kinase reaction buffer (without ATP) (15 ul to 3 ml) were added and the combination incubated for 30 minutes.

TABLE 1

| | Concentration | Pretreatment hair follicle length (mm) | Post-treatment hair follicle length (mm) | Hair Growth (mm) | % Inhibition |
|---|---|---|---|---|---|
| Control (for 1–3) | | 4.4 ± .27 | 5.5 ± .25 | 1.1 | 0.00 |
| 1. Tryphostin A48 | 500 μM | 3.2 ± .16 | 3.3 ± .16 | 0.1 | 91 |
| 2. Erbstatin | 500 μM | 3.6 ± .13 | 3.9 ± .10 | 0.3 | 73 |
| 3. Lavendustin A | 50 μM | 3.5 ± .11 | 3.5 ± .12 | 0 | 100 |
| Control (for 4,5) | | 3.3 ± .20 | 4.3 ± .25 | 1.0 | 0.00 |
| 4. methyl caffeate | 500 μM | 3.5 ± .18 | 4.1 ± .17 | 0.6 | 40 |
| 5. Tryphostin AG 1478 | 250 μM | 3.2 ± .23 | 3.8 ± .19 | 0.6 | 40 |

The test solutions were washed with wash buffer, and 100 ul of substrate solution were added to each and incubated in the dark for 6 minutes. 100 ul of stop solution were added, and the UV absorbance read at 450 nm. The increase in UV absorbance at 450 nm provided a measure of the enzyme activity.

The ability of protein-tyrosine kinase inhibitors to inhibit the skin/hair follicle enzyme activity was determined by measuring protein-tyrosine kinase activity in the presence and absence of the inhibitor. For enzyme inhibition studies, the inhibitor was added to the reaction mixture at a concentration of 1 mM following addition of the enzyme sample. The results are shown in Table 3.

TABLE 3

| Inhibitor | Concentration | % Inhibition |
| --- | --- | --- |
| Tryphostin A47 | 1 mM | 16% |
| Herbimycin | 1 mM | 37% |
| HNMPA(AM)$_3$ | 1 mM | 66% |
| Methyl caffeate | 1 mM | 100% |
| N-acetyl-Asp-Tyr-(2-malonyl)-Val-pro-Met-Leu-NH$_3$ | 1 mM | 83% |
| Lavendustin A | 1 mM | 59% |

HNMPA(AM)$_3$: Hydroxy-2-naphthalenylmethylphosphonic acid tris acetoxymethyl ester

What is claimed is:

1. A method of reducing mammalian androgen-stimulated hair growth which comprises
   selecting an area of skin from which reduced androgen-stimulated hair growth is desired; and
   applying to said area of skin a dermatologically acceptable composition comprising an inhibitor of protein-tyrosine kinase in an amount effective to reduce androgen-stimulated hair growth.
2. The method of claim 1, wherein the protein-tyrosine kinase is an EGF receptor.
3. The method of claim 1, wherein said inhibitor is lavendustin-A.
4. The method of claim 1, wherein said inhibitor is erbstatin.
5. The method of claim 1, wherein said inhibitor is a tryphostin.
6. The method of claim 1, wherein said inhibitor is piceatannol.
7. The method of claim 1, wherein said inhibitor is 4-hydroxybenzylidenemalononitrile.
8. The method of claim 1, wherein said inhibitor is 3,5-di-t-butyl-4-hydroxy-benzylidenemalononitrile.
9. The method of claim 1, wherein said inhibitor is α-cyano-(3,4-dihydroxy)cinnamonitrile.
10. The method of claim 1, wherein said inhibitor is α-cyano-(3,4,5-trihydroxy)cinnamonitrile.
11. The method of claim 1, wherein said inhibitor is α-cyano-(3,4-dihydroxy)cinnamide.
12. The method of claim 1, wherein said inhibitor is α-cyano-(3,4-dihydroxy)thiocinnamide.
13. The method of claim 1, wherein said inhibitor is 2-amino-4-(4'-hydroxyphenyl)-1,1,3-tricyanobuta-1,3-diene.
14. The method of claim 1, wherein said inhibitor is 2-amino-4-(3',4',5'-trihydroxyphenyl)-1,1,3-tricyanobuta-1,3-diene.
15. The method of claim 1, wherein said inhibitor is 2-amino-4-(1HA-indol-5-yl)-1,1,3-tricyanobuta-1,3-diene.
16. The method of claim 1, wherein said inhibitor is 4-hydroxy-3-methoxy-5-(benzothiazolythiomethyl) benzllidenecyanoacetamide.
17. The method of claim 1, wherein said inhibitor is 4-amino-N-(2,5-dihydroxybenzyl)methyl benzoate.
18. The method of claim 1, wherein said inhibitor is 4-(3-chloroanilino)-6,7-dimethoxyquinazoline.
19. The method of claim 1, wherein said inhibitor is α-cyano-(3,4-dihydroxy)-N-benzylcinnamide.
20. The method of claim 1, wherein said inhibitor is (–)-R-N-(a-methylbenzyl)-3,4-dihdroxybenzylidenecyano acetamide.
21. The method of claim 1, wherein said inhibitor is α-cyano-(3,4-dihydroxy)-N-(3-phenylpropyl)cinnamide.
22. The method of claim 1, wherein said inhibitor is α-cyano-(3,4-dihydroxy)-N-phenylcinnamide.
23. The method of claim 1, wherein said inhibitor is α-cyano-(+)-(S)-N-(α-phenethyl)-(3,4-dihydroxy) cinnamide.
24. The method of claim 1, wherein said inhibitor is α-cyano-(3,4-dihydroxy)-N-(phenylbutyl)cinnamide.
25. The method of claim 1, wherein said inhibitor is herbimycin A.
26. The method of claim 1, wherein said inhibitor, is a thiazolidine-dione.
27. The method of claim 1, wherein said inhibitor is phenazocine.
28. The method of claim 1, wherein said inhibitor is a 2,3-dihydro-2-thioxo-1H-indole-3-alkanoic acid.
29. The method of claim 1, wherein said inhibitor is a 2,2'-dithiobis-1H-indole-3-alkanoic acid.
30. The method of claim 1, wherein said inhibitor is a sulfonylbenzoyl-nitrostyrene.
31. The method of claim 1, wherein said inhibitor is methyl caffeate.
32. The method of claim 1, wherein said inhibitor is hydroxy-2-naphthalenylmethylphosphonic acid tris acetoxymethyl ester.
33. The method of claim 1, wherein the concentration of said inhibitor of said composition is between 0.1% and 30%.
34. The method of claim 1, wherein the inhibitor provides a reduction in hair growth of at least 20% when tested in the Human Hair Follicle Growth assay.
35. The method of claim 1, wherein the inhibitor provides a reduction in hair growth of at least 70% when tested in the Human Hair Follicle Growth assay.
36. The method of claim 1, wherein the inhibitor is applied to the skin in an amount of from 10 to 3000 micrograms of said inhibitor per square centimeter of skin.
37. The method of claim 1, wherein said mammal is a human.
38. The method of claim 37, wherein said area of skin is on the face of the human.
39. The method of claim 38, wherein the composition is applied to the area of skin in conjunction with shaving.
40. The method of claim 37, wherein said area of skin is on a leg of the human.
41. The method of claim 37, wherein said area of skin is on an arm of the human.
42. The method of claim 37, wherein said area of skin is in an armpit of the human.
43. The method of claim 37, wherein said area of skin in on the torso of the human.
44. The method of claim 1, wherein the composition is applied to an area of skin of a woman suffering from hirsutism.
45. The method of claim 1, wherein the composition further includes a second component that also causes a reduction in hair growth.
46. A method of reducing mammalian androgen-stimulated hair growth which comprises
   inhibiting protein tyrosine kinase comprising applying to an area of skin from which reduced androgen-stimulated hair growth is desired an inhibitor of protein tyrosine kinase in an amount effective to reduce androgen-stimulated hair growth.

* * * * *